United States Patent
El-Mallakh

(10) Patent No.: US 6,352,540 B1
(45) Date of Patent: Mar. 5, 2002

(54) DELIVERY DEVICE

(76) Inventor: Maher El-Mallakh, 98 El Hegaz Street, Helipolis, Cairo (EG)

( * ) Notice: Subject to any disclaimer, the term of this patent is extended or adjusted under 35 U.S.C. 154(b) by 0 days.

(21) Appl. No.: 09/639,199

(22) Filed: Aug. 15, 2000

(51) Int. Cl.[7] .............................................. A61B 17/42
(52) U.S. Cl. ...................... 606/123; 606/119; 606/121
(58) Field of Search .................................. 606/119, 121, 606/123, 122, 124, 125, 126, 127, 205; 604/74, 149, 902

(56) References Cited

U.S. PATENT DOCUMENTS 5,224,947 A * 7/1993 Cooper et al. ............... 606/123
5,578,043 A * 11/1996 Galstian ...................... 606/119

* cited by examiner

Primary Examiner—Pedro Philogene
(74) Attorney, Agent, or Firm—Andrus, Sceales, Starke & Sawall, LLP

(57) ABSTRACT

A device for assisting the delivery of a baby. The device comprises a cup having a rim arranged to engage, in use, with the head of a baby. A conduit is attached to the cup and, in use, to a vacuum generating pump to generate a cup-retaining vacuum in the cup. A disk is suspended centrally within the cup by plural force absorbing members, such as springs or elastic members, and is used for absorbing forces that are not perpendicular to the plane of the head engaging rim of the cup during use.

7 Claims, 3 Drawing Sheets

DELIVERY DEVICE

BACKGROUND OF THE INVENTION

The present invention relates to a device for assisting in the delivery of a baby during labour.

Devices for assisting in baby delivery are well known. One well known device is the "ventouse vacuum cup device".

Such a device generally consists of a cup, the rim of which engages the head of a baby. A vacuum is generated within the cup so that force can be applied to the baby's head via the cup.

This device, whilst useful in providing withdrawal force and rotational force when the fetal head has an incorrect orientation, has a number of disadvantages. Firstly, the cup associated with the device can become dislodged if it is incorrectly placed, turned incorrectly or if the head of the baby is hairy, and the vacuum generated in the cup fails and/or if the cup is subjected to non-perpendicular forces. Secondly, it is possible to unintentionally apply excessive force to the head during employment of the device. Furthermore, accurate location of the cup requires considerable skill and experience and is generally only therefore used by a skilled operator.

SUMMARY OF THE INVENTION

According to the present invention there is provided a device for assisting the delivery of a baby, the device comprising:

- a cup having a rim arranged to engage, in use, with the head of a baby;
- a conduit attached to the cup and, in use, to a vacuum generating pump to generate a cup-retaining vacuum in the cup; and
- means for absorbing forces that are not perpendicular to the plane of the head-engaging rim of the cup applied to the cup during use.

The cup may have a rubber seal around its head-engaging rim, in order to reduce the likelihood of the seal between the head and the cup being broken during use.

The means for absorbing forces applied to the head via the cup may comprise a disk to which a handle is connected in use, the disk being suspended centrally within the cup by plural force absorbing members, such as springs or elastic members. The disk may have one or more handle engaging members formed thereon.

A device may also be provided with a handle for use by an operator during operation of the device. The handle may be arranged such that it disengages with the device if excessive force is applied to it.

One example of the present invention will now be described with reference to the accompanying drawings, in which:

DESCRIPTION OF THE PREFERRED EMBODIMENT

Figure 1:
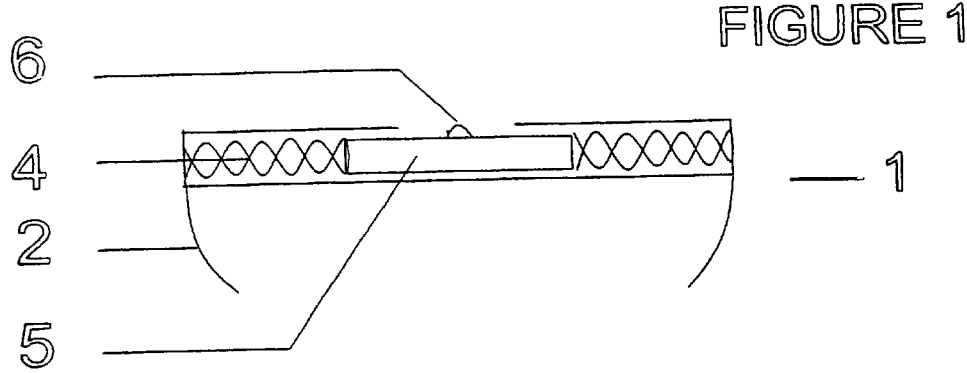
FIG. 1 is a side cross-sectional view of a device according to the present invention.
Figure 2:
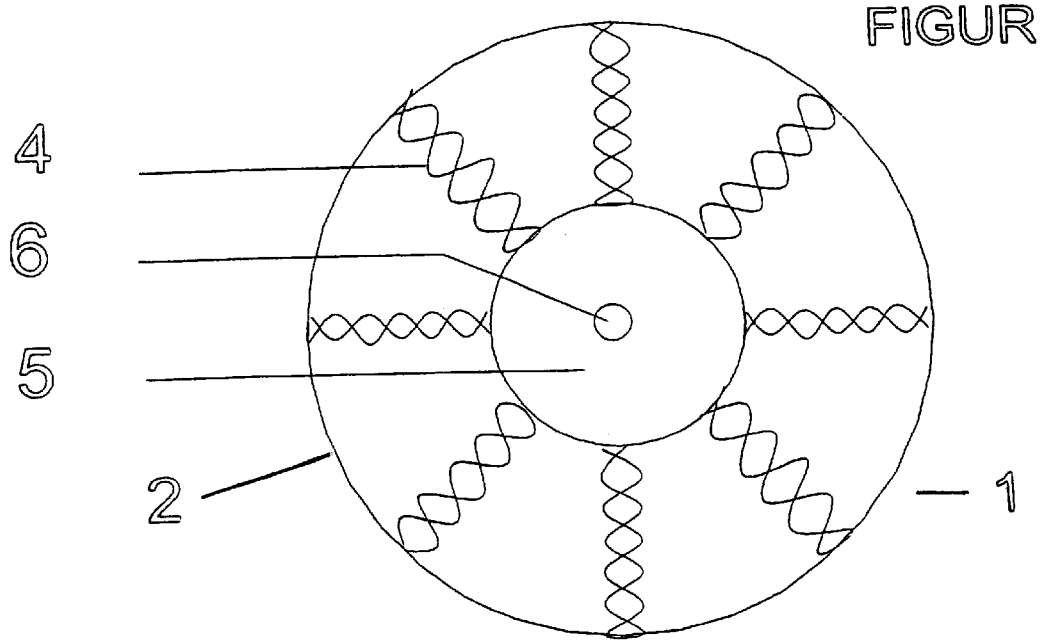
FIG. 2 is a plan cross-sectional view of the present invention.
Figure 3:
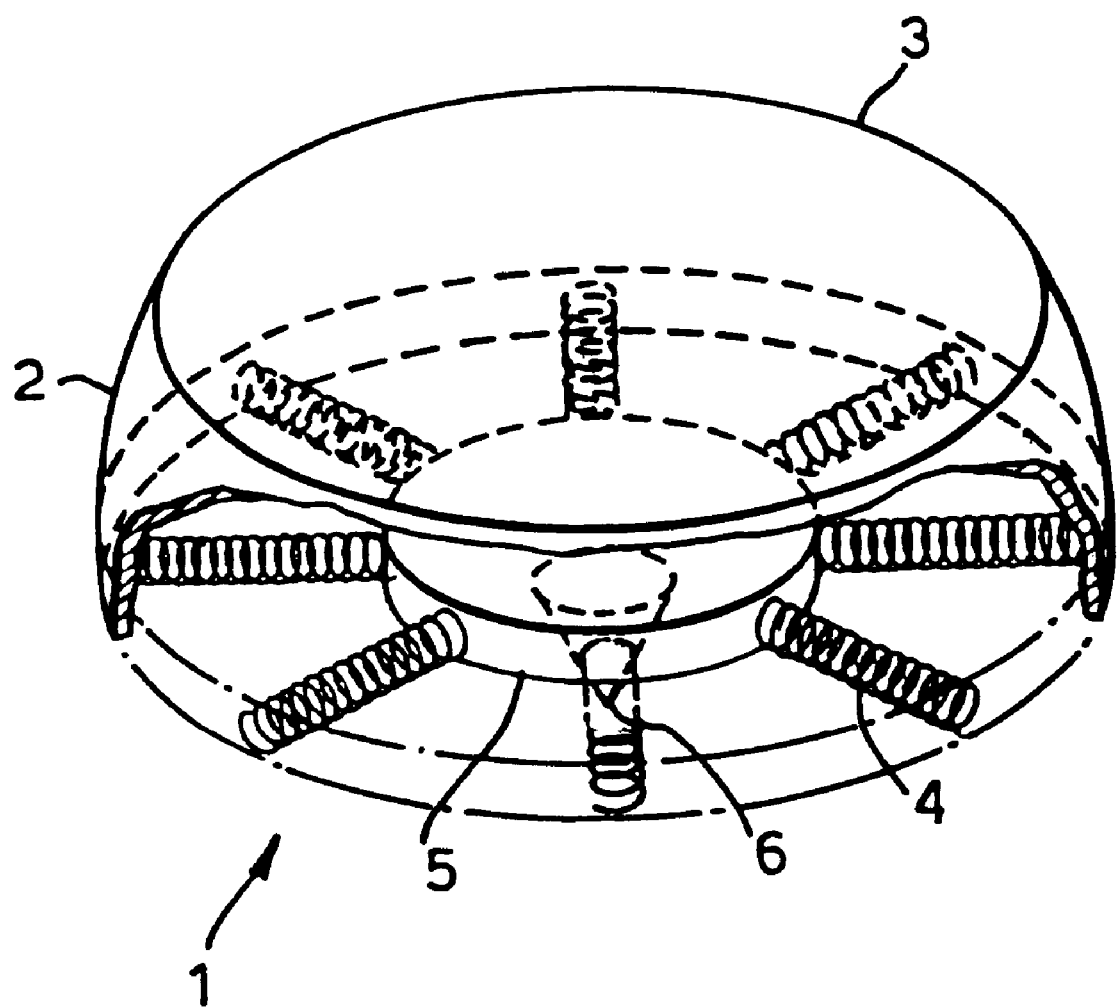
FIG. 3 is a side perspective view of a cup employed in the present invention.
Figure 4:
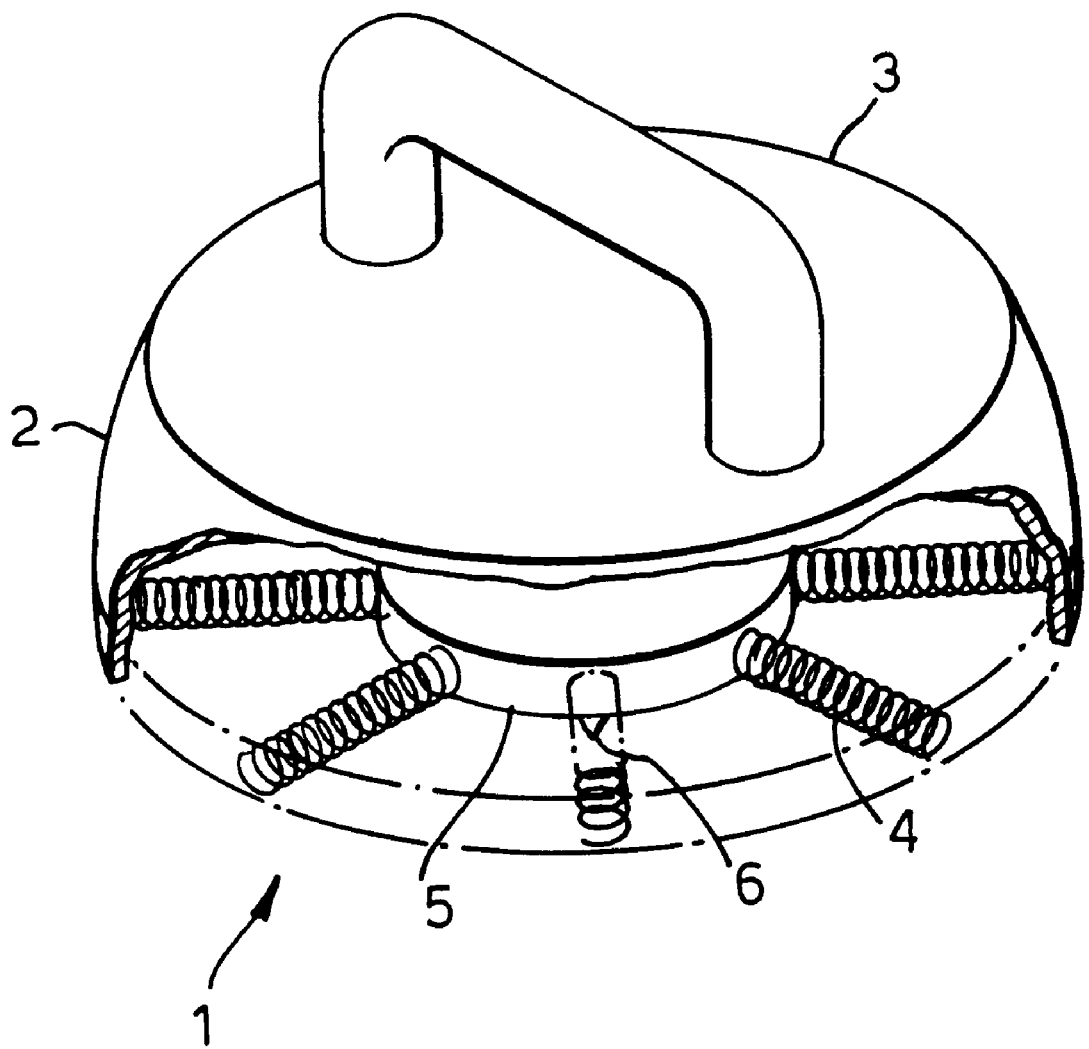
FIG. 4 is a side perspective view of the cup illustrating a handle for use by an operator of the cup.

Referring to FIG. 1, a delivery device according to the present invention has a cup 2, formed from metal or plastic, and having a diameter of approximately 5 cm. In use, the rim 3 of the cup 2 engages with the head of a baby. The rim 3 may be formed from an elastomer to ensure a good air-tight seal. The interior of the cup 2 is attached, via a conduit (not shown), to a vacuum pump (not shown). When the cup 2 is in position the pump generates a vacuum within the cup 2 to retain the cup 2 on the head.

Positioned within the cup 2 is a disk 5, which is disposed centrally within the cup and retained in position by plural elastic members 4, which in this example are simple metal springs. Positioned at the center of the disk, and also central to the cup 2, is a handle engaging member 6 which, in use, engages with a handle 8.

In use, the disk 5 and elastic members 4 act in combination to disperse any forces not perpendicular to the rim 3 of the cup 2. This prevents incorrect forces being applied to the head, and also ensures that such forces do not cause release of the cup 2 from the head.

So that excessive transverse or radial forces are not applied a handle (not shown) is provided for engagement with member 6. The handle is used by an operator during operation of the device and is arranged to release from member 6 under application of excessive force.

What is claimed is:

1. A device for assisting the delivery of a baby, the device comprising:

- a cup having a rim arranged to engage, in use, with the head of a baby;
   - a conduit attached to the cup and, in use, to a vacuum generating pump to generate a cup-retaining vacuum in the cup; and
   - means for absorbing forces that are not perpendicular to the plane of the head-engaging rim of the cup applied to the cup during use.

2. A device according to claim 1, where the cup has a rubber seal around its head-engaging rim.

3. A device according to claim 1, wherein the means for absorbing forces applied to the head via the cup comprises a disk to which a handle is connected in use, the disk being suspended centrally within the cup by plural force absorbing members.

4. A device according to claim 3, wherein the disk has one or more handle engaging members formed thereon.

5. A device according to claim 1 provided with a handle for use by an operator during operation of the device, the handle being arranged such that it disengages with the device if excessive force is applied to it.

6. A device according to claim 3, wherein said force absorbing members are springs.

7. A device according to claim 3, wherein said force absorbing members are elastic members.

* * * * *